US012059285B2

(12) United States Patent
Gao et al.

(10) Patent No.: US 12,059,285 B2
(45) Date of Patent: Aug. 13, 2024

(54) HYBRID LINEARIZATION SCHEME FOR X-RAY CT BEAM HARDENING CORRECTION

(71) Applicant: RefleXion Medical, Inc., Hayward, CA (US)

(72) Inventors: Hewei Gao, Dublin, CA (US); Zhihui Sun, San Jose, CA (US)

(73) Assignee: RefleXion Medical, Inc., Hayward, CA (US)

( * ) Notice: Subject to any disclaimer, the term of this patent is extended or adjusted under 35 U.S.C. 154(b) by 637 days.

(21) Appl. No.: 17/220,443

(22) Filed: Apr. 1, 2021

(65) Prior Publication Data
US 2021/0307713 A1     Oct. 7, 2021

Related U.S. Application Data

(60) Provisional application No. 63/006,513, filed on Apr. 7, 2020.

(51) Int. Cl.
*A61B 6/00* (2024.01)
*A61B 6/03* (2006.01)
(Continued)

(52) U.S. Cl.
CPC ............ *A61B 6/5258* (2013.01); *A61B 6/032* (2013.01); *A61B 6/4435* (2013.01); *A61B 6/582* (2013.01);
(Continued)

(58) Field of Classification Search
CPC ..... A61B 6/5258; A61B 6/032; A61B 6/4435; A61B 6/582; G06T 11/005; G06T 11/008;
(Continued)

(56) References Cited

U.S. PATENT DOCUMENTS

| 3,794,840 A | 2/1974 | Scott |
| 5,636,299 A | 6/1997 | Bueno et al. |

(Continued)

FOREIGN PATENT DOCUMENTS

WO    WO-2019237179 A1 * 12/2019 ............. A61B 6/032

OTHER PUBLICATIONS

Blake, S.J. et al. (2013). "Characterization of a novel EPID designed for simultaneous imaging and dose verification in radiotherapy," *Med. Phys.* 40:091902-1-091902-11.
(Continued)

*Primary Examiner* — Nancy Bitar
*Assistant Examiner* — Heath E. Wells
(74) *Attorney, Agent, or Firm* — Cooley LLP

(57) ABSTRACT

Disclosed herein are methods for reducing beam-hardening artifacts in CT imaging using a mapping operator that comprises a hybrid spectral model that incorporates air scan X-ray intensity data acquired at two different effective mean energies. In one variation, the air scan X-ray intensity data acquired during a calibration session is combined with an ideal spectral model for each X-ray detector to derive the hybrid spectral mode. A mapping operator based on the hybrid spectral model is used to correct beam-hardening artifacts in the acquired CT projection data. In some variations, the mapping operator is a lookup table of monochromatic (corrected) projection values, and the acquired CT projection data is used to calculate the index of the lookup table entry that contains the corrected projection value that corresponds with the acquired CT projection data.

9 Claims, 8 Drawing Sheets

(51) Int. Cl.
    *A61B 6/58*     (2024.01)
    *G06T 11/00*     (2006.01)

(52) U.S. Cl.
    CPC .......... *G06T 11/005* (2013.01); *G06T 11/008* (2013.01); *G06T 2211/408* (2013.01)

(58) Field of Classification Search
    CPC ......... G06T 2211/408; G06T 2211/424; G06T 2211/448
    See application file for complete search history.

(56) References Cited

U.S. PATENT DOCUMENTS

| | | | |
|---|---|---|---|
| 5,784,432 | A | 7/1998 | Kurtz et al. |
| 5,864,146 | A | 1/1999 | Karellas |
| 5,886,783 | A | 3/1999 | Shapanus et al. |
| 8,610,077 | B2 | 12/2013 | Beaulieu et al. |
| 9,242,120 | B2 | 1/2016 | Verhaegen et al. |
| 9,265,971 | B2 | 2/2016 | Baltes et al. |
| 9,364,186 | B2 | 6/2016 | Nioutsikou |
| 9,770,603 | B2 | 9/2017 | Da Silva Rodrigues et al. |
| 10,695,586 | B2 | 6/2020 | Harper et al. |
| 10,775,517 | B2 | 9/2020 | Maolinbay |
| 11,300,692 | B2 | 4/2022 | Maolinbay |
| 11,714,202 | B2 | 8/2023 | Maolinbay |
| 2006/0159223 | A1 | 7/2006 | Wu et al. |
| 2009/0014662 | A1 | 1/2009 | Suhami |
| 2013/0156163 | A1 | 6/2013 | Liu et al. |
| 2018/0204356 | A1* | 7/2018 | Xia .......... A61B 6/582 |
| 2018/0242939 | A1* | 8/2018 | Kang .......... A61B 6/482 |
| 2022/0326402 | A1 | 10/2022 | Maolinbay |

OTHER PUBLICATIONS

International Search Report mailed on Jan. 6, 2017, for PCT Application No. PCT/US2016/051750, filed on Sep. 14, 2016, 4 pages.
International Search Report mailed on Jul. 16, 2021, for PCT Application No. PCT/US2021/025421, filed on Apr. 1, 2021, 3 pages.
Mijnheer, B. et al. (2013). 3D EPID-based in vivo dosimetry for IMRT and VMAT, 7$^{th}$ International Conference on 3D Radiation Dosimetry (IC3DDose), IOP Publishing, J. Physics: Conference Series 444, pp. 1-7.
Non-Final Office Action mailed on Aug. 27, 2019, for U.S. Appl. No. 15/921,219, filed Mar. 14, 2018, 17 pages.
Non-Final Office Action mailed on Jun. 14, 2021, for U.S. Appl. No. 16/993,029, filed Aug. 13, 2020, 12 pages.
Notice of Allowance mailed on May 27, 2020, for U.S. Appl. No. 15/921,219, filed Mar. 14, 2018, 9 pages.
Notice of Allowance mailed on Dec. 16, 2021, for U.S. Appl. No. 16/993,029, filed Aug. 13, 2020, 9 pages.
Notice of Allowance mailed on Mar. 7, 2023, for U.S. Appl. No. 17/711,606, filed Apr. 1, 2022, 11 pages.
Ruchti, R.C. (1996). "The use of scintillating fibers for charged-particle tracking," *Annu. Rev. Nucl. Part. Sci.* 46:281-319.
Star-Lack, J. et al. (2015). "A piecewise-focused high DQE detector for MV imaging," *Med. Phys.* 42:5084-5099.
Steciw, S. et al. (2005). "Three-dimensional IMRT verification with a flat-panel EPID," *Med. Phys.* 32:600-612.
Teymurazyan, A. et al. (2012). "Monte Carlo simulation of a novel water-equivalent electronic portal imaging device using plastic scintillating fibers," *Med. Phys.* 39:1518-1529.
Wang, Y. et al. (2009). "High-DQE EPIDs based on thick, segmented BGO and CsI:TI scintillators: performance evaluation at extremely low dose," *Med. Phys.* 36:5707-5718.
Wendling, M. et al. (2006). "Accurate two-dimensional IMRT verification using a back-projection EPID dosimetry method," *Med. Phys.* 33:259-273.
Written Opinion of the International Searching Authority mailed on Jan. 6, 2017, for PCT Application No. PCT/US2016/051750, filed on Sep. 14, 2016, 6 pages.
Written Opinion of the International Searching Authority mailed on Jul. 16, 2021, for PCT Application No. PCT/US2021/025421, filed on Apr. 1, 2021, 5 pages.
Corrected Notice of Allowability mailed on Jun. 13, 2023, for U.S. Appl. No. 17/711,606, filed Apr. 1, 2022, 2 pages.

* cited by examiner

200

| | |
|---|---|
| Acquire a first set of X-ray intensity data for each X-ray detector in the imaging system during an air scan at a first effective mean energy | 202 |

↓

| | |
|---|---|
| Acquire a second set of X-ray intensity data for each X-ray detector in the imaging system during an air scan at a second effective mean energy | 204 |

↓

| | |
|---|---|
| Calculate a virtual filter for each X-ray detector in the imaging system using the first and second sets of X-ray intensity data | 206 |

↓

| | |
|---|---|
| Calculate a mapping operator for each X-ray detector in the imaging system, where the mapping operator includes a hybrid spectral model that uses the virtual filter to convert a polychromatic projection value to a monochromatic projection value | 208 |

↓

| | |
|---|---|
| Generate a lookup table having $k$ corrected projection values ($p_m$) for each X-ray detector in the imaging system, where each of the $k$ corrected projection values are calculated from a discrete set of $k$ polychromatic projection values ($p_p^{discrete}$) each separated by a discretization step size ($s$) using the mapping operator | 210 |

Calculate a low-to-high ratio (LHR) of the X-ray intensity data measured at a first lower effective mean energy $I^i_{lower}$ to the X-ray intensity data measured at a second higher effective mean energy $I^i_{higher}$ for each of the ($i$) X-ray detectors in the imaging system:

$$LHR^i_{meas} = \frac{I^i_{lower}}{I^i_{higher}}$$

302

---

Set a spectral model of the X-ray intensity at each of the first and second effective mean energies to the measured LHR for each of the ($i$) X-ray detectors:

$$LHR^i_{meas} = \frac{\int S^i_{eff-L}(E)\exp(-\mu_{vir}(E)T^i_{vir})\,dE}{\int S^i_{eff-H}(E)\exp(-\mu_{vir}(E)T^i_{vir})\,dE}$$

Where:
$S^i_{eff-L}(E)$ is the spectrum of the imaging system at the 1st effective energy
$S^i_{eff-H}(E)$ is the spectrum of the imaging system at the 2nd effective energy
$\mu_{vir}(E)$ is an attenuation coefficient of virtual filter of a selected material
$T^i_{vir}$ is a thickness of the virtual filter of the selected material

304

---

Calculate the thickness $T^i_{vir}$ for each X-ray detector using a first-order Taylor expansion:

$$LHR^i_{meas} \approx \frac{\int S^i_{eff-L}(E) \times (1-\mu_{vir}(E)T^i_{vir})\,dE}{\int S^i_{eff-H}(E) \times (1-\mu_{vir}(E)T^i_{vir})\,dE}$$

$$T^i_{vir} \approx \frac{\int S^i_{eff-L}(E)\,dE - LHR^i_{meas}\int S^i_{eff-H}(E)\,dE}{\int S^i_{eff-L}(E)\mu_{vir}(E)\,dE - LHR^i_{meas}\int S^i_{eff-H}(E)\mu_{vir}(E)\,dE}$$

Calculate the hybrid spectral model $mS_{eff}(E)$ for each X-ray detector by modifying an ideal spectral model $S_{eff}(E)$ with a virtual filter that represents the variability of each X-ray detector:

$$mS_{eff}(E) = S_{eff}(E)\exp(-\mu_{vir}(E) \times \alpha T^i_{vir})$$

Where:
$T^i_{vir}$ is the thickness of the virtual filter for the $i^{th}$ X-ray detector made of a selected material,
$\mu_{vir}(E)$ is an attenuation coefficient of virtual filter of the selected material, and
$\alpha$ is an optional scaling factor

402

Iteratively calculate, for each X-ray detector, a monochromatic projection value ($p_m$) that corresponds to a polychromatic projection value ($p_p$) based on the following spectral model:

$$p_p = -ln\left(\frac{\int mS_{eff}(E)\exp(-\mu'_{obj}(E)\, p_m)\, dE}{\int mS_{eff}(E)\, dE}\right)$$

Where:
$p_m$ is $\mu_{obj}(\overline{E})D_{obj}$
$\mu'_{obj}(E)$ is $\frac{\mu_{obj}(E)}{\mu_{obj}(\overline{E})}$

404

Generate a mapping operator (e.g., lookup table) for each X-ray detector that maps up to $k$ monochromatic projection values ($p_m$) to $k$ polychromatic projection values ($p_p$) such that:

$$p_m = LUT(j) = LUT(^{p_p}/_s)$$

where the $k$ monochromatic projection values ($p_m$) are calculated from a discrete set of $k$ polychromatic projection values ($p_p$) each separated by a discretization step size ($s$), where $j$ is a LUT index

| Calculate an index value based on the acquired CT projection data for each X-ray detector in the imaging system | 612 |

↓

| Identify, using the index value, the corrected projection value in a lookup table containing a plurality of projection values calculated using a hybrid spectral model | 614 |

| Calculate an index value ($j$) by dividing the acquired CT projection data ($p_p$) of each X-ray detector in the imaging system by a discretization step size ($s$): $$j = \frac{p_p}{s}$$ | 622 |

↓

| Determine the corrected projection value ($p_m$) by identifying the $j^{th}$ entry in a lookup table that contains up to $k$ corrected projection values calculated from a discrete set of $k$ polychromatic projection values each separated by the discretization step size ($s$) using a hybrid spectral model | 624 |

FIG. 6C

FIG. 7A
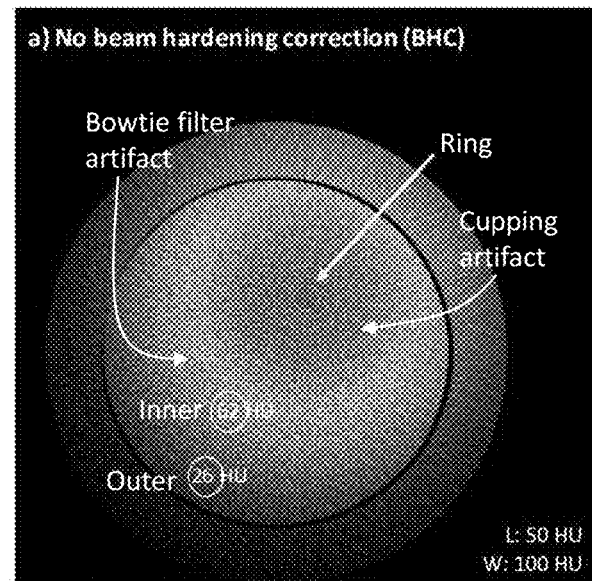
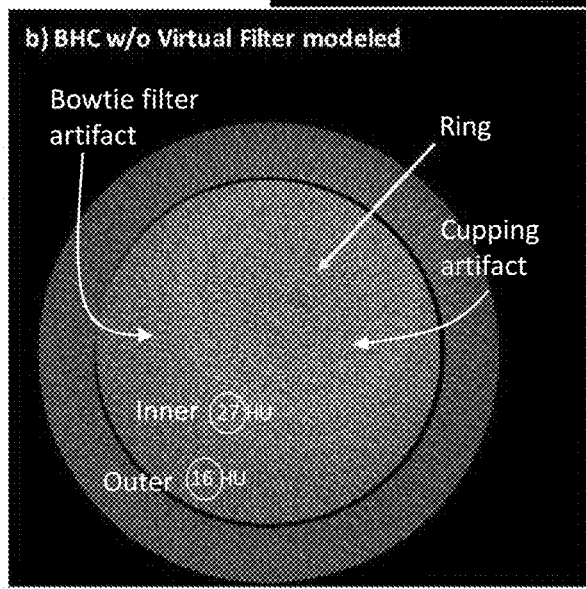
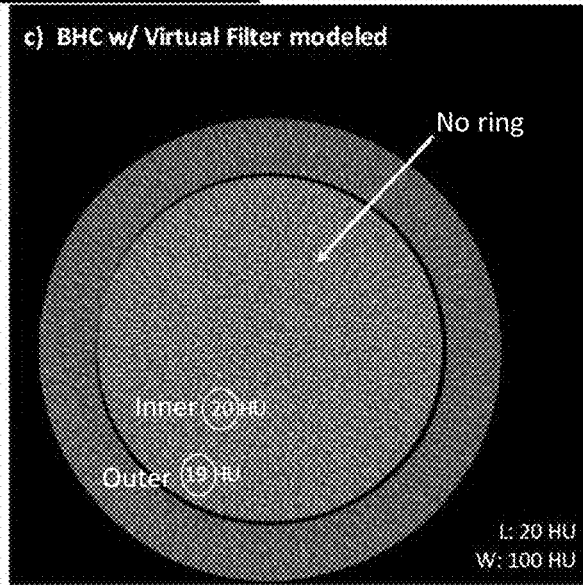
FIG. 7B
FIG. 7C

HYBRID LINEARIZATION SCHEME FOR X-RAY CT BEAM HARDENING CORRECTION

CROSS-REFERENCE TO RELATED APPLICATIONS

This application claims priority to U.S. Provisional Patent Application No. 63/006,513 filed Apr. 7, 2020, the disclosure of which is hereby incorporated by reference in its entirety.

BACKGROUND

X-ray computed tomography (CT) imaging systems comprise an array of X-ray detectors located across from an X-ray source, and can generate images of an object located between the X-ray source and detectors based on the attenuation of X-rays through the object. The X-ray detectors are located at various angular positions relative to the object. CT images represent the attenuation properties of the object and can be determined by measuring the intensity of the X-rays that are incident on the detectors. Ideally, X-ray attenuation is linear, so that the X-ray intensity measured at the detectors is linearly related to the attenuation property of the object. However, because the X-ray source for CT system is typically a polychromatic radiation source, it emits photons with different energies, and photons with different energies are attenuated differently from each other as they pass through an object. In many materials, lower energy photons are attenuated more than higher energy photons. This non-uniform attenuation across different photon energies may cause the edges of an object to appear brighter than the central portion of the object (even when it is made of a homogenous material) because the lower energy photons are more attenuated at the central portion of the object than at its edges. The imaging artifacts that arise from this non-linear attenuation are called beam-hardening artifacts. Typically, beam-hardening artifacts are corrected by collecting X-ray detector data during a calibration session using a number of phantoms made of different materials with different thicknesses to generate a mapping function that maps the polychromatic projection data to the ideal or corrected monochromatic projection values. However, this type of calibration and artifact correction method can be tedious and time-consuming, as it requires multiple CT scans of multiple phantoms having different dimensions and/or materials.

In addition, images reconstructed from CT imaging systems where the X-ray source and the array of X-ray detectors are rotated during image acquisition (e.g., X-ray source and detectors are mounted on a rotating gantry) may be particularly sensitive to the different spectral characteristics or responses of the individual X-ray detectors.

As such, it is desirable to improve CT imaging system calibration methods to help address beam-hardening artifacts and/or compensate for the variable spectral responses of the individual X-ray detectors in the detector array.

SUMMARY

Disclosed herein are methods for reducing beam-hardening artifacts in CT imaging using a mapping operator that comprises a hybrid spectral model that incorporates air scan X-ray intensity data acquired at two different effective mean energies. A mapping operator may be calculated for each X-ray detector of a CT imaging system. The mapping operator may be used to convert the acquired CT projection data (which is calculated based on the output signal from its corresponding X-ray detector) to a corrected projection value. In some variations, the mapping operator may comprise a lookup table (LUT), and the acquired CT projection data is used to calculate a lookup table index that may be used to identify the corrected projection value that corresponds with the acquired CT projection data.

Also disclosed herein are phantom-less calibration methods for reducing beam-hardening artifacts. The X-ray intensity data acquired during a calibration session may be used to generate a hybrid spectral model that maps polychromatic projection data to calculated monochromatic projection values. The hybrid spectral model includes an ideal spectral model that is combined with air scan X-ray intensity data acquired at two different effective mean energies. The hybrid spectral model is used to generate a mapping operator that may be used during a CT scan to convert the acquired CT projection data to a corrected projection value that may then be used for the CT image reconstruction. During a calibration session, a CT imaging system may acquire a first set of X-ray intensity data during a first air scan at a first effective mean energy and a second set of X-ray intensity data during a second air scan at a second effective mean energy that is higher than the first effective mean energy. The X-ray intensity data for the first and second air scans may be acquired and stored for each X-ray detector, and for rotatable CT imaging systems, X-ray intensity data may be acquired while the CT imaging system rotates through multiple angles. A CT imaging system controller may then calculate a virtual filter for each X-ray detector using the first and second sets of X-ray intensity data. In some variations, the virtual filter may be characterized by a selected filter material (e.g., aluminum) and a filter thickness, and the first and second sets of X-ray intensity data may be used to calculate the thickness of the virtual filter for each X-ray detector in the array. The CT imaging system controller may then calculate a mapping operator for each X-ray detector that uses a hybrid spectral model that combines the virtual filter with an ideal spectral model. The mapping operator represents the relationship between polychromatic projection data derived from acquired X-ray detector intensity data and a corrected projection value. The corrected projection value may also be referred to as a monochromatic projection value, since the corrected projection value approximates the projection value of a monochromatic X-ray source (i.e., emitting photons of a single energy level or light of a single wavelength), which has little or no beam-hardening artifacts.

One variation of a method for reducing a beam-hardening artifact in CT imaging may comprise acquiring CT projection data at each X-ray detector in a CT imaging system, determining a corrected projection value for each of the acquired CT projection data using a mapping operator that comprises a hybrid spectral model that incorporates air scan CT projection data acquired at two different effective mean energies, and generating an artifact-corrected CT image by combining the corrected projection value of each of the acquired CT projection data. The hybrid spectral model may represent the acquired CT projection data $p_p$ as a function of a corrected projection value $p_m$ and may include a virtual filter calculated based on the acquired air scan X-ray intensity data. The mapping operator may comprise a lookup table LUT for each X-ray detector in the CT imaging system, where each lookup table LUT may contain k corrected projection values $p_m$ that correspond to discretized values of CT projection data $p_p^{discrete}$ that are separated by a discretization step size s. The discretized values of CT projection data may be derived by multiplying lookup table index j by the discretization step size s, and determining a corrected projection value $p_m$ may comprise calculating the lookup table index j based on the acquired CT projection data $p_p$. In some variations, calculating the lookup table index j may comprise dividing the acquired CT projection data $p_p$ by the discretization step size s, and determining the corrected projection value may comprise identifying the corrected projection value $p_m$ that corresponds with the lookup table index j:

$$j = \frac{p_p}{s}$$
$$p_m = LUT(j)$$

In some variations, the lookup table may be a first lookup table LUT_1 for a first CT scan energy level and the mapping operator may comprise a second lookup table LUT_2 for a second CT scan energy level, where the second lookup table LUT_2 may contains k' corrected projection values $p'_m$ that correspond to discretized values of CT projection data $p'_p{}^{discrete}$ that are separated by a discretization step size s'. Determining the corrected projection value $p_m$ for the acquired CT projection data $p_p$ may comprise calculating the corrected projection value $p_m$ using the hybrid spectral model by iterating though different values of $p_m$ to attain a CT projection value that approximates the acquired CT projection data $p_p$. For example, calculating the corrected projection value $p_m$ using the hybrid spectral model may comprise iterating though different values of $p_m$ using Newton's method to determine the value of $p_m$ that results in a projection value that best approximates the acquired CT projection data $p_p$.

In some variations, a plurality of hybrid spectral models may be calculated for different CT scan energy levels. In one variation, the hybrid spectral model may be a first hybrid spectral model for a first CT scan energy level and the mapping operator may comprise a second hybrid spectral model for a second CT scan energy level. Determining the corrected projection value $p_m$ for the acquired CT projection data $p_p$ may comprise identifying the CT scan energy level at which the CT projection data was acquired, and calculating the corrected projection value $p_m$ using the hybrid spectral model corresponding to the identified CT scan energy level.

In some variations, air scan X-ray intensity data may be acquired at a first effective mean energy and at a second effective mean energy. For example, the first energy may be 80 kVp and the second energy may be 140 kVp, and CT projection data acquisition may be at an energy level of 120 kVp.

One variation of a method for phantom-less calibration of a CT imaging system to reduce beam-hardening artifacts may comprise acquiring a first set of X-ray intensity data for each X-ray detector of a CT imaging system during a first air scan at a first effective mean energy, acquiring a second set of X-ray intensity data for each X-ray detector of the CT imaging system during a second air scan at a second effective mean energy that is higher than the first effective mean energy, calculating a virtual filter for each X-ray detector of the CT imaging system using the first and second set of X-ray intensity data, and calculating a mapping operator for each X-ray detector of the CT imaging system, where the mapping operator comprises a hybrid spectral model that uses the virtual filter to convert a polychromatic projection value to a monochromatic projection value. Each virtual filter may be made of a selected material and have a thickness. Calculating the virtual filter for each X-ray detector may comprise calculating the thickness of the virtual filter. In some variations, calculating a mapping operator may comprise generating a lookup table LUT having k monochromatic projection values $p_m$ that have been calculated from a discrete set of k polychromatic projection values $p_p{}^{discrete}$ each separated by a discretization step size s using the hybrid spectral model. Optionally, in some variations, the lookup table is a first lookup table LUT_1 for a first CT scan energy level, and the mapping operator may further comprise a second lookup table LUT_2 for a second CT scan energy level. In this variation, the method may further comprise calculating k' monochromatic projection values $p'_m$ that have been calculated from a second discrete set of k' polychromatic projection values $p'_p{}^{discrete}$ each separated by a discretization step size s' using the hybrid spectral model.

In some variations, calculating the virtual filter thickness for each of i X-ray detectors may comprise calculating a low-to-high ratio ($LHR_{meas}{}^i$) of the X-ray intensity data ($I_{lower}{}^i$) acquired at the first lower effective mean energy to the X-ray intensity data acquired at the second higher effective mean energy ($I_{higher}{}^i$):

$$LHR_{meas}^i = \frac{(I_{lower}^i)}{(I_{higher}^i)}$$

and calculating the thickness ($T_{vir}{}^i$) of the virtual filter for each of the i X-ray detectors, $$T_{vir}^i \approx \frac{\int S_{eff-L}^i(E)dE - LHR_{meas}^i \int S_{eff-H}^i(E)dE}{\int S_{eff-L}^i(E)\mu_{vir}(E)dE - LHR_{meas}^i \int S_{eff-H}^i(E)\mu_{vir}(E)dE}$$

where
$S_{eff-L}{}^i(E)$ is a spectrum of the CT imaging system at the first lower effective mean energy,
$S_{eff-H}{}^i(E)$ is a spectrum of the CT imaging system at the second higher effective mean energy, and
$\mu_{vir}(E)$ is an attenuation coefficient of virtual filter of the selected material.

The hybrid spectral model $mS_{eff}{}^i(E)$ may be a combination of an ideal spectral model $S_{eff}{}^i(E)$ and the virtual filter having the thickness ($T_{vir}{}^i$) and the attenuation coefficient $\mu_{vir}(E)$:

$$mS_{eff}^i(E) = S_{eff}^i(E)\exp(-\mu_{vir}(E) \times \alpha T_{vir}^i)$$

where $\alpha$ is a scaling factor.

In some variations, calculating the mapping operator may comprise iteratively calculating a monochromatic projection value ($p_m$) that corresponds to a polychromatic projection value ($p_p$) based on the hybrid spectral model:

$$p_p = -\ln\left(\frac{\int mS_{eff}^i(E)\exp(-\mu'_{obj}(E)p_m)dE}{\int mS_{eff}^i(E)dE}\right)$$

where $\mu'_{obj}(E)$ is a normalized attenuation coefficient $$\left(\frac{\mu_{obj}(E)}{\mu_{obj}(\overline{E})}\right)$$

of a scanning subject. In some examples, $\mu'_{obj}(E)$ is a normalized attenuation coefficient of water, $\mu_{vir}(E)$ is the attenuation coefficient of aluminum, and the scaling factor $\alpha$ is 1.

In some variations, the CT imaging system may comprise a rotatable gantry, an imaging X-ray source mounted to the gantry, and the X-ray detectors may be mounted to the gantry opposite the imaging X-ray source, and wherein acquiring the first set of X-ray intensity data comprises rotating the gantry during the first air scan. Acquiring the second set of X-ray intensity data may comprise rotating the gantry during the second air scan. In some examples, the first energy may be 80 kVp and the second energy may be 140 kVp.

BRIEF DESCRIPTION OF THE DRAWINGS

FIG. 2 is a flowchart representation of one variation of a calibration method.

FIG. 3 is a flowchart representation of one variation of a method for calculating a virtual filter.

FIG. 4 is a flowchart representation of one variation of a method for generating a mapping operator using a hybrid spectral model.

FIG. 6B is a flowchart representation of one variation of a method for determining the corrected projection value using a lookup table.

FIG. 6C is a flowchart representation of one variation of a method for determining a corrected projection value with a lookup table.

FIGS. 7A-7C are CT images of a phantom. FIG. 7A depicts an image where the acquired CT projection data was not corrected for beam-hardening artifacts. FIG. 7B depicts an image where the acquired CT projection data was corrected for beam-hardening artifacts using an ideal spectral model that does not include a virtual filter. FIG. 7C depicts an image where the acquired CT projection data was corrected for beam-hardening artifacts using a hybrid spectral model with a virtual filter.

DETAILED DESCRIPTION

Figure 1:
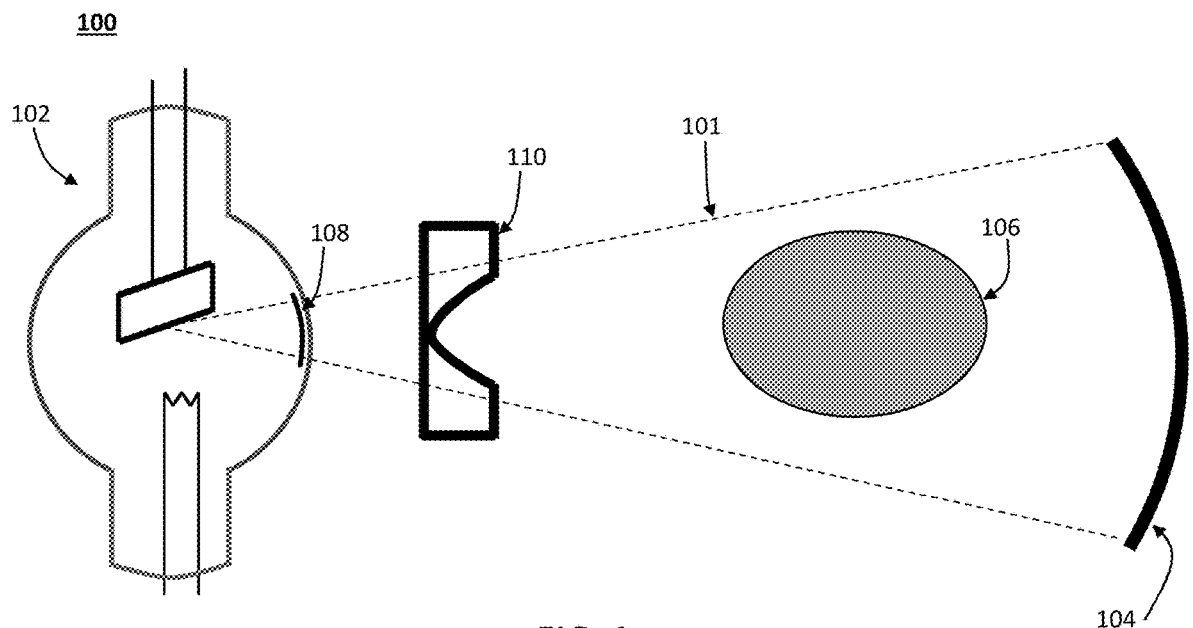
FIG. 1 a schematic depiction of one variation of a CT imaging system.

Disclosed herein are methods for reducing beam-hardening artifacts in CT imaging using a mapping operator that comprises a hybrid spectral model that incorporates air scan X-ray intensity data acquired at two different effective mean energies. The air scan X-ray intensity data may be acquired during a calibration session and combined with an ideal spectral model for each X-ray detector to derive the hybrid spectral model (i.e., a "hybrid" or combination of an ideal spectral model and empirical data). The combination of acquired air scan X-ray intensity data with an ideal spectral model may simulate the unique variabilities in each of X-ray detectors, so that the hybrid spectral model may provide a better approximation of the projection data from the X-ray detectors. With the hybrid spectral model, a mapping operator may be generated that relates the projection data calculated from intensity data from an X-ray detector (which may be subject to beam-hardening artifacts due to the polychromatic X-ray source) with a corrected projection value that represents a detector response in the absence of beam-hardening artifacts. The projection data calculated from X-ray intensity data may also be referred to as polychromatic projection data. The corrected projection value may also be referred to as a monochromatic projection value, since it approximates the projection value of a CT system with a monochromatic X-ray source (which would not have beam-hardening artifacts in the CT projection data). In some variations, the mapping operator may be a lookup table (LUT), and the polychromatic projection data may be used to calculate a table index that is used to identify the corresponding monochromatic (i.e., corrected) projection value that has been calculated using the hybrid spectral model. The CT imaging system controller may then combine the corrected projection value of each X-ray detector in the array of X-ray detectors to generate a CT image with little or no beam-hardening artifacts.

In some variations, air scan X-ray intensity data acquired at two different effective mean energies for each X-ray detector may be used to calculate a virtual filter for that X-ray detector. The virtual filter represents or approximates the spectral variabilities of X-ray detectors in their sensitivity and response to incident photons that may arise, for example, due to manufacturing variations, unique structural characteristics. A virtual filter may also represent or approximate the spectral variabilities of individual X-ray detectors due to their different locations relative to the X-ray source. In a CT imaging system, the array of X-ray detectors are located across from the X-ray source, and may span across the expected field-of-view provided by the X-ray source radiation beam (e.g., for a fan-shaped radiation beam, the array of X-ray detectors may be arranged along an arc that corresponds with the fan-shaped beam). In some variations, a bowtie filter may be located in front of the X-ray source and because the central portion of the filter is thinner than the peripheral portions of the filter, the spectral properties of the radiation incident on X-ray detectors that are located in a central portion of the radiation beam may be different from the spectral properties of the radiation incident on X-ray detectors located in the periphery of the radiation beam. For example, the X-ray intensity data (and corresponding projection data) from X-ray detectors in the periphery of the detector array may be subject to more beam-hardening effects from bowtie filter than the X-ray intensity data (and corresponding projection data) from X-ray detectors in the center of the array. The virtual filters for each X-ray detector calculated from the calibration air scans may account for these differences, resulting in a hybrid spectral model that better approximates the actual spectrum of the incident radiation and the X-ray detector's output than a spectral model without a virtual filter.

As used throughout this document, "projection data" represents the degree to which X-rays that pass through a material (e.g., material of a scanned object) are attenuated. A projection data value may be a quantity that is indicative of the attenuation strength of the material; that is, how much the energy and/or intensity of an X-ray is reduced as it passes through the material. A CT image is a combination (e.g., a reconstruction) of the projection data collected from the X-ray detectors in the detector array. Projection data may be calculated from the intensity data acquired by an X-ray detector. For example, the intensity data acquired by an X-ray detector in the presence of a scan object (I), and the intensity data acquired by the X-ray detector in the absence of the scan object ($I_0$) may be used to calculate the CT projection data (p) for that X-ray detector:

$$p = -\ln\left(\frac{I}{I_0}\right)$$

Acquired CT projection data (or acquired projection data) may refer to projection data calculated based on the intensity data measured by an X-ray detector. Because this acquired projection data is calculated based on actual intensity measurements from an X-ray detector, it may be affected by beam-hardening effects. Without beam-hardening corrections, the combination of (e.g., reconstruction from) the acquired projection data over all the X-ray detectors of the detector array may result in an image with beam-hardening artifacts. In a CT imaging system where the imaging radiation source is a polychromatic X-ray source, the acquired CT projection data may also be referred to as polychromatic projection data ($p_p$).

Corrected projection values may refer to projection values calculated based on the hybrid spectral model as described herein, where beam-hardening artifacts and/or spectral variabilities of individual X-ray detectors are reduced or eliminated. The corrected projection value may also be referred to as a monochromatic projection value ($p_m$), since it approximates the projection value of a CT system with a monochromatic X-ray source.

While the beam-hardening correction and calibration methods disclosed herein are described in the context of a CT imaging system with a rotatable polychromatic X-ray source and an array of X-ray detectors that rotate in concert with the X-ray source, it should be understood that these methods may also be used in non-rotatable CT imaging systems, for example, linearly-translating CT imaging systems where the X-ray source and detectors are stepped along the scan object, as well as CT imaging systems where the detectors are stationary (e.g., a full 360° ring, multiple arcs around a circumference of a stationary frame or gantry) and the X-ray source is rotatable (e.g., mounted on a rotatable gantry). The example systems provided herein comprise a polychromatic X-ray source that emits fan-beam radiation, but the same methods may be used with systems comprising a parallel-beam and/or a cone-beam polychromatic X-ray source. The beam-hardening correction and calibration methods described herein may be used with stand-alone CT imaging systems as well as CT imaging systems that are part of a radiotherapy system. For example, these methods may be used to calibrate and generate CT images of a radiotherapy system comprising a CT imaging system (e.g., with a rotatable imaging radiation source and detectors, and a CT imaging system controller), and a therapeutic radiation source that is movable about a patient. The therapeutic radiation source may be mounted on a rotatable and/or extendable C-arm, an articulated robotic arm, and/or a rotatable circular gantry. Some variations of a radiotherapy system may optionally comprise another array of X-ray detectors across from the therapeutic radiation source. One example of a radiotherapy system may comprise a CT imaging system and a therapeutic radiation source both mounted on a rotatable gantry. The rotatable gantry may be configured to rotate rapidly, for example, from about 20 RPM to about 70 RPM, e.g., about 60 RPM. In some variations, a radiotherapy system may comprise a CT imaging system, a therapeutic radiation source both mounted on a rotatable gantry, and one or more arrays of PET detectors, which may optionally be mounted on the same rotatable gantry. Additional details of various radiotherapy systems may be found in U.S. patent application Ser. No. 15/814,222 filed Nov. 15, 2017, which is hereby incorporated by reference in its entirety.

Systems

FIG. 1 is a schematic depiction of one variation of a CT imaging system (100). A CT imaging system (100) may comprise an X-ray source (102), an array (104) of X-ray detectors, and a CT imaging system controller (not shown) in communication with the X-ray source (102) and the array (104) of X-ray detectors. In some variations, the X-ray source (102) may be a polychromatic X-ray source, which may be configured to emit X-rays across a spectrum of X-ray energies. The data output from each of the X-ray detectors in the array may represent the intensity value(s) of the X-rays incident upon each of the X-ray detectors. The X-ray source (102) and the array (104) of X-ray detectors may be mounted on a rotatable gantry, which may be configured to rotate about a scan object (106) and acquire X-ray intensity data from various angles. In some variations, the CT imaging system may comprise a housing that encloses the X-ray source, the detector array, and the rotatable gantry, and where the housing may be shaped to define a bore through which a scan platform may be moved. The scan platform may be moved along the longitudinal central axis of the bore, which may also be the axis of rotation of the rotatable gantry.

A CT imaging system may also comprise one or more spectral components disposed in the X-ray source beam path. The one or more spectral components may be configured to modify the spectral characteristics of the radiation beam (101) that is transmitted through the scan object (106), which may be a patient. For example, a CT imaging system may comprise one or more filters, some which may be intrinsic to the X-ray source, while others may be separate from, or external to, the X-ray source. There may optionally be one or more filters and/or collimators disposed over the X-ray detectors, which may help to remove scattered radiation and/or select for certain spectral characteristics. In the variation depicted in FIG. 1, the X-ray source (102) may have one or more intrinsic filters (108). An optional bowtie filter (110) may be disposed in the radiation beam path (101), external to the X-ray source (102). In some variations, the scan object 106 may be located in a bore of the CT-imaging system, and there may be a bore window (not show) in the radiation beam path (i.e., through which the radiation beam passes after it emerges from the bowtie filter). The X-ray spectrum of the a polychromatic X-ray source may be represented by X-ray tube spectrum S(E), the attenuation of the intrinsic filters (108) may be represented by exp ($-\mu_{int}(E)T_{int}$), and the attenuation of the bowtie filter (110) may be represented by exp ($-\mu_{bow}(E)T_{bow}$), and the attenuation of the bore window may be represented by exp ($-\mu_{bore}(E)T_{bore}$). The energy response of an X-ray detector in the array may be represented by E ($1-\exp(-\mu_{det}(E)T_{det})$).

The coefficient μ is an attenuation coefficient of that particular spectral component (which may vary depending on the material that comprises the spectral component or in the case of the detector, the detector scintillator), and the quantity T represents the thickness of the component (or path length traveled by an X-ray through the component). The attenuation coefficient μ and the thickness T may be known as part of the system design, which designates the materials and dimensions (i.e., overall geometry and placement) of each component. The X-ray tube spectrum S(E) may also be known or characterized using simulations and/or measured.

A model of the effective spectrum $S_{eff}(E)$ of the CT imaging system (100) without a scan object (106) in the bore, may be expressed as Equation (1):

$$S_{eff}(E)=S(E)\exp(-\mu_{int}(E)T_{int})\exp(-\mu_{bow}(E)T_{bow})$$
$$\exp(-\mu_{bore}(E)T_{bore})E(1-\exp(-\mu_{det}(E)T_{det}))$$

As described previously, due to the differing relative location of each X-ray detector (i.e., the $i^{th}$ X-ray detector in the array) relative to the X-ray source, the effective spectrum at each X-ray detector may be different $S_{eff}^{i}(E)$. Notably, the model of the effective spectrum of the CT system as a whole (Equation 1) and at each individual X-ray detector $S_{eff}^{i}(E)$ does not account for the variabilities that may arise due to manufacturing variations and/or any random system variances, such as the varying inefficiencies of individual X-ray detectors to convert photons into electrical signals.

Methods

Methods for correcting beam-hardening artifacts may comprise generating a hybrid spectral model for each X-ray detector that accounts for the variability of that X-ray detector. In some variations, the variability of an individual X-ray detector may be represented by a virtual filter that is made of a selected material and having a thickness such that the attenuation of X-rays through the virtual filter approximates the variability in that X-ray detector's spectral response. One or more of the parameters of the virtual filter, such as the material of the filter and/or its thickness, may be determined using X-ray intensity data acquired during a calibration session. The empirical data acquired during a calibration session may reflect the actual spectral response of the individual X-ray detectors in the detector array, and may be combined with an ideal spectral model to generate a hybrid spectral model that better approximates the actual response of the individual X-ray detectors.

One variation of a calibration method may comprise acquiring X-ray intensity data using the X-ray detectors in the detector array at two different effective mean energies of the imaging X-ray source. In some variations, the X-ray source and the array of X-ray detectors may rotate about the bore of the system and acquire X-ray intensity data at multiple angles around the bore. For example, X-ray intensity data may be acquired for each X-ray detector at up to about 1200 locations around the scan region, e.g., from about 4 locations (0°, 90°, 180°, 270°) to about 360 locations, from about 370 locations to about 700 locations, from about 800 locations to about 1000 locations, about 720 locations, 960 locations, etc., over one or more rotations about the scan region (e.g., from 1 rotation to about 200 rotations about the scan region). The X-ray intensity data may be acquired without an object in the scan region, i.e., an air scan.

The X-ray intensity data acquired during a calibration session may then be used to calculate a virtual filter for the individual X-ray detectors that models the variability of that X-ray detector. The virtual filter may be combined with an ideal spectral model for the individual X-ray detector to generate a hybrid spectral model for that X-ray detector. The hybrid spectral model may then be used to calculate a mapping operator for an individual X-ray detector that represents the relationship between polychromatic projection data (i.e., acquired CT projection data that may include beam-hardening artifacts and individual X-ray detector variabilities) and a corresponding monochromatic projection value (i.e., a corrected projection value that has reduced or eliminated beam-hardening artifacts and/or X-ray detector variabilities). The mapping operator may be applied to CT projection data obtained by individual X-ray detectors during a patient imaging session to determine the corresponding corrected projection values. The corrected projection values may then be used to reconstruct a CT image where the beam-hardening artifacts are reduced or removed.

One variation of a calibration method for acquiring X-ray intensity data that may be incorporated into a hybrid spectral model that may be used for the correction (e.g., reduction) of beam-hardening artifacts is depicted in FIG. 2. Calibration method (200) may comprise acquiring (202) a first set of X-ray intensity data for each X-ray detector in the imaging system during an air scan at a first effective mean energy, acquiring (204) a second set of X-ray intensity data for each X-ray detector in the imaging system during an air scan at a second effective mean energy, calculating (206) a virtual filter for each X-ray detector in the imaging system using the first and second sets of X-ray intensity data, and calculating (210) a mapping operator for each X-ray detector in the imaging system, where the mapping operator includes a hybrid spectral model that uses the virtual filter to convert a polychromatic projection value to a monochromatic projection value. While the acquisition of X-ray intensity data (202, 204) may be done as an air scan, i.e., without a phantom in the scan region, in other variations, the X-ray intensity data may be acquired at two different effective mean energies with a phantom in the scan region. The first and second sets of X-ray intensity data may comprise X-ray intensity data acquired from multiple angles about the scan region. For example, for a CT imaging system where the X-ray source and/or the X-ray detectors are mounted on a movable (e.g., rotatable) gantry, the X-ray intensity data for an individual detector may be acquired from multiple angles, and optionally, over multiple rotations about the scan region. For example, the acquisition of X-ray intensity data (202, 204) may occur over at least one rotation of the X-ray source and/or the X-ray detectors about the scan region, and in some variations, X-ray intensity data may be acquired over two or more rotations of the X-ray source and/or the X-ray detectors about the scan region. Calculating (208) a mapping operator for each X-ray detector may comprise calculating a different mapping operator for each CT scan energy level that may be used during an imaging session. For example, if it is desired to calibrate the CT imaging system to allow the user to conduct an imaging scan at a first scan energy level (e.g., 80 kVp) and conduct an imaging scan at a second scan energy level (e.g., 120 kVp), calculating (208) a mapping operator may comprise calculating a first mapping operator for the first scan energy level and calculating a second mapping operator for the second scan energy level. The first and second mapping operators for each X-ray detector may be stored in a memory of the CT imaging system controller. During an imaging session, when the user selects the desired scan energy level, the CT imaging system controller may be configured to select between the two mapping operators (i.e., select the mapping operator that has been calculated for that scan energy level) for converting the acquired CT projection data to the corrected projection values.

Method (200) may optionally further comprise generating (210) a lookup table having k corrected projection values ($p_m$) for each X-ray detector in the imaging system, where each of the k corrected projection values are calculated from a discrete set of k polychromatic projection values ($p_p^{discrete}$) each separated by a discretization step size (s) using the mapping operator. As described above, in the variation where CT imaging scans may be conducted at two different scan energy levels, two different mapping operators and two different lookup tables may be generated and stored in the memory of the CT imaging system controller. During an imaging session, when the user selects the desired scan energy level, the CT imaging system controller may be configured to select the lookup table that corresponds to the selected scan energy level for converting the acquired CT projection data to the corrected projection values.

As described previously, a virtual filter may be characterized by a selected filter material (e.g., aluminum, graphite) and a filter thickness. The attenuation properties of the filter material and the thickness of the filter along the X-ray beam (e.g., beam path length) may approximate or represent the spectral response variabilities of X-ray detectors, for example, variations in their sensitivity and response to incident photons that may arise, for example, due to manufacturing variations and/or the location of an individual X-ray detector relative to the X-ray source of the CT imaging system. One variation of a method for calculating a virtual filter is depicted in FIG. 3. Method (300) may be performed by the CT imaging system controller after X-ray intensity data has been acquired (e.g., as described above with regard to steps 202 and 204, and depicted in FIG. 2). Method (300) may comprise calculating (302) a low-to-high ratio (LHR) of the X-ray intensity data measured at a first lower effective mean energy $I_{lower}^i$ to the X-ray intensity data measured at a second higher effective mean energy $I_{higher}^i$ for each of the (i) X-ray detectors in the imaging system:

$$LHR_{meas}^i = \frac{I_{lower}^i}{I_{higher}^i}$$

Method (300) may then comprise setting (304) a spectral model of the X-ray intensity at each of the first and second effective mean energies to the measured LHR for each of the (i) X-ray detectors. The X-ray intensity data measured at an individual X-ray detector may be an integration of the ideal effective spectrum $S_{eff}^i(E)$ (see Equation 1) adjusted by a virtual filter having attenuation coefficient $\mu_{vir}(E)$, which is determined by the attenuation properties of the selected virtual filter material, and a virtual filter thickness $T_{vir}^i$, which may vary across individual X-ray detectors. That is:

$$I_i = \int S_{eff}^i(E) \exp(-\mu_{vir}(E) T_{vir}^i)$$

Setting (304) the spectral model of the X-ray intensity data at each of the first and second effective mean energies to the measured LHR of an individual X-ray detector may be as follows:

$$LHR_{meas}^i = \frac{\int S_{eff-L}^i(E) \exp(-\mu_{vir}(E) T_{vir}^i) dE}{\int S_{eff-H}^i(E) \exp(-\mu_{vir}(E) T_{vir}^i) dE}$$

where:

$S_{eff-L}^i(E)$ is the spectrum of the imaging system at the i-th X-ray detector at the $1^{st}$ effective mean energy; and $S_{eff-H}^i(E)$ is the spectrum of the imaging system at the i-th X-ray detector at the $2^{nd}$ effective energy, which is, in this example, higher than the first effective mean energy.

Method (300) may then comprise calculating (306) the thickness $T_{vir}^i$ for the individual X-ray detectors in the detector array. The quantities $LHR_{meas}^i$, $S_{eff-L}^i(E)$, $S_{eff-H}^i(E)$, and $\mu_{vir}(E)$ may be measured or known based on material properties, and based on these quantities, $T_{vir}^i$ may be found. In one variation, calculating (306) the virtual filter thickness $T_{vir}^i$ may use a first-order Taylor expansion, as follows:

$$LHR_{meas}^i = \frac{\int S_{eff-L}^i(E) \times (1 - \mu_{vir}(E) T_{vir}^i) dE}{\int S_{eff-H}^i(E) \times (1 - \mu_{vir}(E) T_{vir}^i) dE}$$

$$T_{vir}^i \approx \frac{\int S_{eff-L}^i(E) dE - LHR_{meas}^i \int S_{eff-H}^i(E) dE}{\int S_{eff-L}^i(E) \mu_{vir}(E) dE - LHR_{meas}^i \int S_{eff-H}^i(E) \mu_{vir}(E) dE}$$

After the thickness of the virtual filter for an individual X-ray detector has been calculated, the hybrid spectral model $mS_{eff}^i(E)$ for that X-ray detector may be represented by Equation (2):

$$mS_{eff}^i(E) = S_{eff}^i(E) \exp(-\mu_{vir}(E) \times \alpha T_{vir}^i)$$

where $\alpha$ is an optional scaling factor. In this variation, the $\alpha$ scaling factor may be 1. The hybrid spectral model may be used to calculate a mapping operator for converting acquired CT projection data, which may contain beam-hardening artifacts, into corrected projection values.

A different hybrid spectral model may be generated for individual X-ray detectors for different CT scan energy levels. A first hybrid spectral model may be calculated using a first ideal effective spectrum $S_{eff-1}^i(E)$ for the first CT scan energy level, and a second hybrid spectral model may be calculated using a second ideal effective spectrum $S_{eff-2}^i(E)$ for the second CT scan energy level. Each of the first and second hybrid spectral models may be used to calculate first and second mapping operators for individual X-ray detectors (as described further below), which may be stored in a memory of the CT imaging system controller and retrieved during an imaging session.

Methods for Generating a Mapping Operator

FIG. 4 depicts one variation of a method for generating a mapping operator using a hybrid spectral model. Method (400) may comprise calculating (402) a hybrid spectral model $mS_{eff}^i(E)$ for each X-ray detector by modifying an ideal spectral model $S_{eff}^i(E)$ with a virtual filter that represents the variability of each X-ray detector, as represented above in Equation (2), and iteratively calculating (404) for each X-ray detector, a monochromatic projection value ($p_m$) that corresponds to a polychromatic projection value ($p_p$) based on the following spectral model Equation (3):

$$p_p = -\ln\left(\frac{\int mS_{eff}(E) \exp(-\mu_{obj}'(E) p_m) dE}{\int mS_{eff}(E) dE}\right)$$

where $p_m$ is $\mu_{obj}(\overline{E})D_{obj}$, which is a monochromatic projection at a given mean energy $\overline{E}$; and $\mu'_{obj}(E)$ is $$\frac{\mu_{obj}(E)}{\mu_{obj}(\overline{E})},$$

which is a normalized attenuation coefficient calculated by taking the ratio of the attenuation coefficient at each CT scan energy component and the attenuation coefficient at the mean CT scan energy.

Equation (3) may be re-written so that the monochromatic projection value $p_m$ is represented in terms of the polychromatic projection value $p_p$ (i.e., the acquired CT projection data, which is derived from the X-ray intensity data measured at an individual X-ray detector).

Alternatively or additionally, method (400) may comprise generating (406) a mapping operator for each X-ray detector that maps up to k monochromatic projection values $p_m$ to k polychromatic projection values $p_p^{discrete}$. In some variations, the mapping operator may be a lookup table (LUT).

$$p_m = LUT(j)$$

In some variations, the k monochromatic projection values $p_m$ may be calculated from a discrete set of k polychromatic projection values $p_p^{discrete}$, which may each be separated by a discretization step size s. The lookup table index may be calculated by dividing the polychromatic data (i.e., acquired CT projection data):

$$p_m = LUT(j) = LUT(p_p/s)$$

In some variations, a mapping operator (e.g., a lookup table) may be calculated for each desired CT scan energy level based on different hybrid spectral models for each of those CT scan energy levels. Notably, as long as the spectrum of the X-ray source at the different CT scan energy levels is characterized or known (e.g., from technical specifications provided by the manufacturer of the X-ray source or from simulation), no additional X-ray intensity data is required to be collected during a calibration session in order to calculate hybrid spectral models for different CT scan energy levels; the X-ray intensity data acquired during the two air scan at two different effective mean energies are sufficient for generating any number of hybrid spectral models for calculating mapping operators for the desired number of CT scan energy levels. Each of the mapping operators for different CT scan energy levels may be stored in a memory of the CT imaging system controller, and retrieved for correcting beam-hardening artifacts during an imaging session based upon the scan energy levels selected for the imaging session.

Methods for Generating a Beam-Hardening Correction Lookup Table

As described above, a mapping operator, such as a lookup table, for an X-ray detector may contain a set of monochromatic projection values that correspond with a set of polychromatic projection values. The set of polychromatic projection values may approximate the range of CT projection data that may be acquired at that X-ray detector. During an imaging session, the acquired CT projection data $p_p$ may be used to generate a lookup table index to identify the monochromatic projection value in the lookup table that corresponds with the acquired CT projection data $p_p$. Multiple lookup tables may be generated for each X-ray detector, each lookup table corresponding to each of the CT scan energy levels that may be used during an imaging session.

Figure 5A:
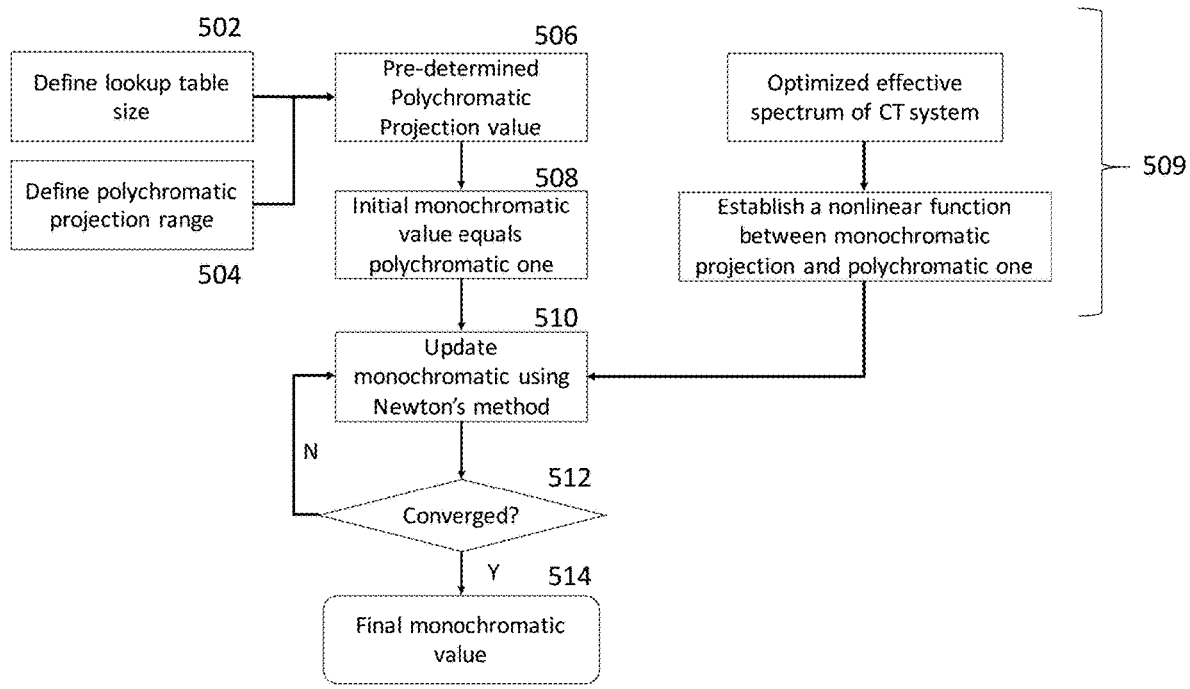
FIG. 5A is a flowchart representation of one variation of a method for calculating a set of corrected or monochromatic projection values from a discrete set of polychromatic projection values.
Figure 5B:
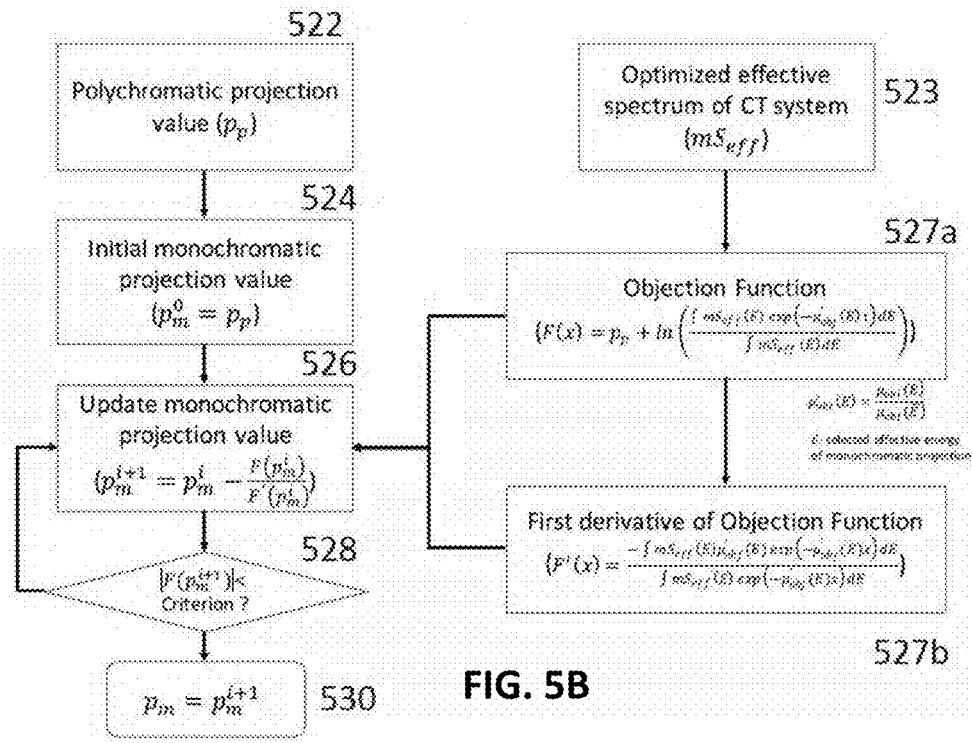
FIG. 5B is a flowchart representation of one variation of a method of using Newton's method in conjunction with a hybrid spectral model to calculate a monochromatic projection value that corresponds with a selected polychromatic projection value.

One variation of a method for a beam-hardening correction lookup table is represented in FIGS. 5A-5B. FIG. 5A depicts one variation of a method for calculating a set of corrected or monochromatic projection values $p_m$ from a discrete set of polychromatic projection values $p_p^{discrete}$. Method (500) may comprise defining (502) the number of entries (i.e., size k) of the lookup table and defining (504) a range of polychromatic projection data that may be covered by the lookup table. The range of polychromatic projection data may approximate or correspond with the range of acquired CT projection data that may be expected at the individual X-ray detector. In some variations, the range of polychromatic projection data may comprise a set of discrete polychromatic projection values, where each polychromatic projection value is separated by a discretization step size s. The maximum polychromatic projection value may be the discretization step size multiplied by the number of lookup table entries, i.e., s×k. The discretization step size s and/or the lookup table size k may each be selected based on the desired precision (e.g., a smaller step size may be more precise than a larger step size) and/or an estimate of the expected range of polychromatic projection values measured at the individual X-ray detector (e.g., with the same discretization step size, a larger table may encompass a greater range of projection values than a smaller table). Method (500) may comprise selecting (506) a first pre-determined polychromatic projection value within the defined range of polychromatic projection data, setting (508) an initial monochromatic projection value to the first pre-determined polychromatic projection value, updating (510) the initial (intermediate) monochromatic projection value using Newton's Method in combination with a hybrid spectral model (509), and determining (512) whether the updated monochromatic projection value makes the polychromatic projection value calculated by Equation (3) converge to the pre-determined polychromatic projection value. Method (500) may comprise iterating (510-512) on the intermediate monochromatic projection value until the intermediate monochromatic projection value makes the polychromatic projection value calculated by Equation (3) converge to the pre-determined polychromatic value within a pre-specified, acceptable tolerance. In some variations, the hybrid spectral model may be represented by Equation (2), and included in a spectral model represented by Equation (3), as previously described. The final monochromatic value (514) may be included in the lookup table as an entry that is linked or associated with the pre-determined polychromatic projection value. Method (500) may comprise repeating these calculations (506-514) for each of the discrete polychromatic projection values in the defined range (504) of polychromatic projection values. As described previously, multiple lookup tables may be generated for each X-ray detector, each lookup table corresponding to a different CT scan energy level that may be used during an imaging session. Method (500) may be used to generate each of the lookup tables (e.g., LUT_1 for CT scan energy level 1, LUT_2 for CT scan energy level 2, LUT_3 for CT scan energy level 3, etc.) for an individual X-ray detector, which may then be stored in a memory of the CT imaging system controller. Each of the plurality of lookup tables may have the same or different number of entries. The discretization step of the discrete polychromatic projection values may be different or the same across all of the lookup tables.

FIG. 5B depicts one variation of a method of using Newton's method in conjunction with a hybrid spectral model (e.g., the hybrid spectral model described herein) to calculate a monochromatic projection value that corresponds with a selected polychromatic projection value, for example, a discrete polychromatic projection value $p_p^{discrete}$ in a set of discrete polychromatic projection values that correspond with a range of polychromatic projection data (e.g., acquired CT projection data). In some variations, the range of polychromatic projection data may comprise a set of discrete polychromatic projection values, where each polychromatic projection value is separated by a discretization step size s, and the calculated monochromatic projections values may be stored in a lookup table with k entries. Method (520) may comprise selecting (522) a polychromatic projection value $p_p$, setting (524) an initial (intermediate) monochromatic projection value to the selected polychromatic projection value ($p_m^0 = p_p$), updating (526) the initial (intermediate) monochromatic projection value using Newton's Method with a hybrid spectral model, and determining (528) whether the updated monochromatic projection value meets a defined criterion. Updating (526) the intermediate monochromatic projection value may comprise defining (527a) an objection function based on a hybrid spectral model (e.g., represented by Equations (2) and (3)), calculating (527b) a derivative of the objection function, and calculating the difference between the intermediate monochromatic projection value and a ratio of the objection function and its derivative.

In some variations, an objection function may be defined in Equation (4):

$$F(x) = p_p + \ln\left(\frac{\int mS_{eff}(E)\exp(-\mu'_{obj}(E)x)dE}{\int mS_{eff}(E)dE}\right)$$

The first derivative of the above objection function is then:

$$F'(x) = p_p + \frac{-\int mS_{eff}(E)\mu'_{obj}(E)\exp(-\mu'_{obj}(E)x)dE}{\int mS_{eff}(E)\exp(-\mu'_{obj}(E)x)dE}$$

Updating the monochromatic value may comprise calculating the following:

$$p_m^{i+1} = p_m^i - \frac{F(p_m^i)}{F'(p_m^i)}$$

The criterion used to determine (528) whether the intermediate monochromatic value sufficiently corresponds with the selected polychromatic projection value may include calculating the value of the objection function as defined by Equation (4) using the updated intermediate monochromatic projection value. For example, the CT imaging system controller may evaluate whether $|F(p_m^{i+1})|$ is less than a specified criterion (e.g., a selected threshold value that is close to zero). Method (500) may comprise determining whether that calculated value is within a desired tolerance of the selected polychromatic projection value. If not, method (520) may comprise iterating (526-528) on the updated intermediate monochromatic projection value until it meets the desired criterion (i.e., is within the desired tolerance of the selected polychromatic projection value). The final monochromatic value (530) may be included in the lookup table as an entry that is linked or associated with the selected polychromatic projection value (522). Method (520) may comprise repeating these calculations (522-530) for each of the discrete polychromatic projection values in the desired range of polychromatic projection values and/or to populate the lookup table with k entries. As described previously, multiple lookup tables may be generated for each X-ray detector, each lookup table corresponding to a different CT scan energy level that may be used during an imaging session. Method (500) may be used to generate each of the lookup tables (e.g., LUT_1 for CT scan energy level 1, LUT_2 for CT scan energy level 2, LUT_3 for CT scan energy level 3, etc.) for an individual X-ray detector, which may then be stored in a memory of the CT imaging system controller. Each of the plurality of lookup tables may have the same or different number of entries. The discretization step of the discrete polychromatic projection values may be different or the same across all of the lookup tables.

Methods for Correcting Beam-Hardening for Image Reconstruction

The mapping operators (e.g., lookup tables) generated during a calibration session as described above may be used during an imaging session to correct artifacts from acquired CT projection data that may arise from beam-hardening effects and/or X-ray detector variabilities. During an imaging session, a user may select the CT scan energy level that may define the photon energy emitted by the imaging X-ray source to the scan object. This selection may also be used by the CT imaging controller system to select the mapping operator (e.g., lookup table) for each X-ray detector. An imaging session may comprise acquiring X-ray intensity data at each individual X-ray data, calculating CT projection data (i.e., polychromatic projection data) based on the acquired X-ray intensity data, and determining the corrected projection value(s) (i.e., monochromatic projection data) using the selected mapping operator for each individual X-ray detector. The corrected projection values across the X-ray detectors in the array may be combined to generate (e.g., used to reconstruct) an image with reduced (or even eliminated) beam-hardening artifacts. In some variations, the mapping operator for each individual X-ray detector may be a lookup table, and the acquired CT projection data may be used to identify the entry in the lookup table that contains the corresponding monochromatic projection value. Alternatively, or additionally, the mapping operator for each individual X-ray detector may be one or more mapping functions that include the hybrid spectral models described herein (e.g., Equations (2)-(4)).

Figure 6A:
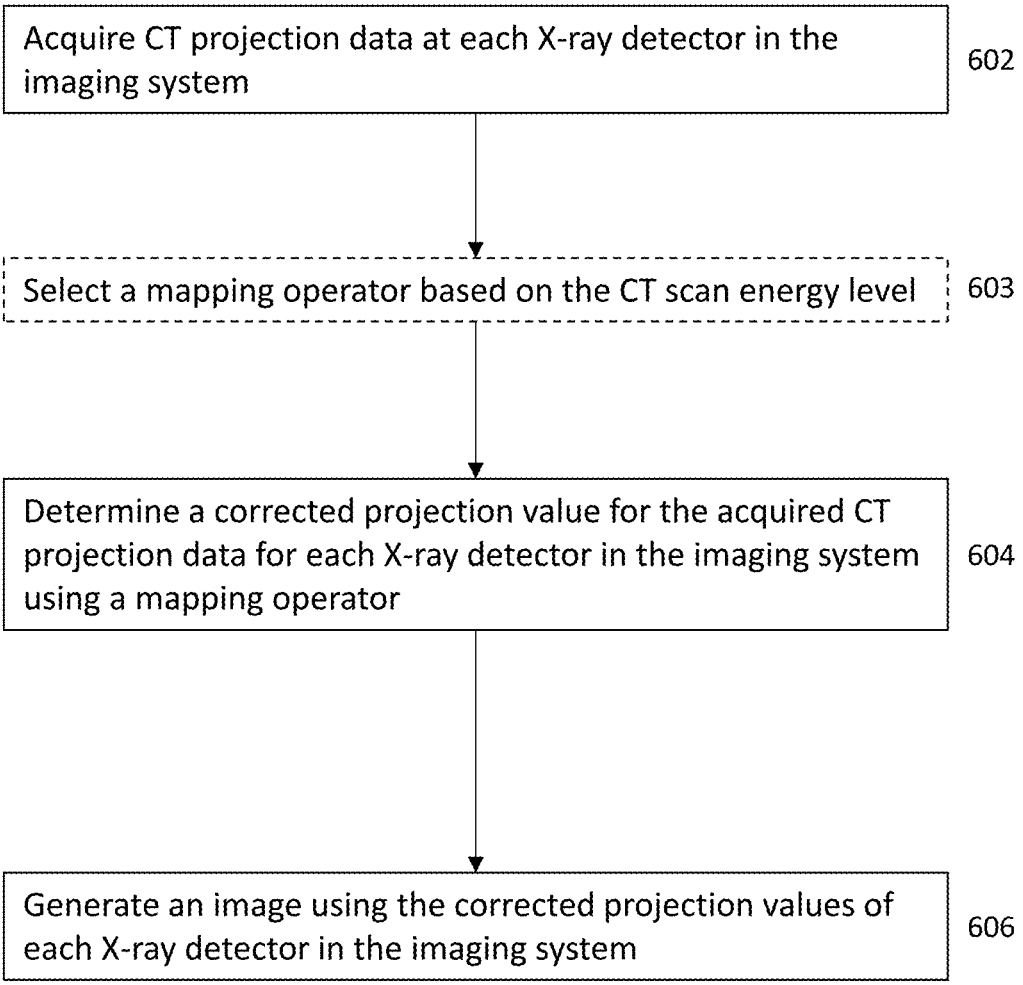
FIG. 6A is a flowchart representation of one variation of a method for correcting beam-hardening artifacts for CT imaging.

FIG. 6A depicts one variation of a method for correcting beam-hardening artifacts for CT imaging. Method (600) may comprise acquiring (602) CT projection data (i.e., polychromatic projection data $p_p$) at each individual X-ray detector in the imaging system, determining (604) a corrected projection value (i.e., monochromatic projection data $p_m$) for the acquired CT projection data for each X-ray detector in the imaging system using a mapping operator, and generating (606) an image using the corrected projection values of each X-ray detector in the imaging system. Acquiring CT projection data may comprise acquiring or measuring X-ray intensity data at an individual X-ray detector, and calculating the acquired CT projection data from the measured X-ray intensity data as described previously, e.g., $$p = -\ln\left(\frac{I}{I_0}\right).$$

Optionally, method (600) may comprise selecting (603) a mapping operator based on the CT scan energy level that will be, or was used, during the imaging session. Each X-ray detector may have one or more mapping operators (e.g., one or more lookup tables) stored in the CT imaging system controller memory that correspond to one or more CT scan energy levels. For example, one or more lookup tables may be generated for each X-ray detector corresponding to one or more CT scan energy levels, and stored in the controller memory. In some variations, the selection of a mapping operator may take place before X-ray intensity data is acquired, or may be after the X-ray intensity data is acquired (e.g., as part of post-processing the acquired intensity data).

In some variations, determining the corrected projection value may use a mapping operator such as a lookup table. FIG. 6B depicts one variation of a method for determining the corrected projection value using a lookup table. Method (610) may comprise calculating (612) an index value based on the acquired CT projection data for each X-ray detector in the imaging system, and identifying (614), using the index value, the corrected projection value in a lookup table containing a plurality of monochromatic projection values calculated using a hybrid spectral model, for example, any of the hybrid spectral models described herein (e.g., that maps a polychromatic projection value to a monochromatic projection value based on two air scan data sets). The lookup table may be generated using one or more of the methods described above.

In some variations, determining the corrected projection value may comprise calculating a lookup table index j from the acquired CT projection data (i.e., polychromatic projection data). FIG. 6C depicts one variation of a method for determining the corrected projection value with a lookup table and using the acquired CT projection data to calculate an index value to identify the table entry with the corresponding corrected projection value. Method (620) may comprise calculating (622) an index value (j) by dividing the acquired CT projection data ($p_p$) of each X-ray detector in the imaging system by a discretization step size (s), i.e.

$$j = \frac{p_p}{s},$$

and determining (624) the corrected projection value ($p_m$) by identifying the $j^{th}$ entry in a lookup table that contains up to k corrected projection values calculated from a discrete set of k polychromatic projection values each separated by the discretization step size (s) using a hybrid spectral model, for example, any of the hybrid spectral models described herein (e.g., that maps a polychromatic projection value to a monochromatic projection value based on two air scan data sets).

Experimental Data

An experiment was conducted using the calibration methods and hybrid spectral models described herein. The results of this experiment are depicted in FIGS. 7A-7C. The experiment was conducted using a CT imaging system comprising a fan-beam imaging X-ray source, and an array of X-ray detectors (each having dimensions of 1.024 mm (width) by 2.213 mm (height), having source-to-detector distance of 1133.4 mm and source-to-isocenter distance of 643 mm. The X-ray source and the detector array are located on a rotatable gantry opposite to each other. The rotatable gantry is configured to rotate up to 60 RPM. The CT imaging system also has a bowtie filter in the imaging beam path. The CT imaging system in this experiment is part of a combined imaging and radiotherapy system, however, a similar experiment could be conducted in a standalone imaging system with the same components as this CT imaging system.

During a calibration session, air scans at 80 kVp and 140 kVp were conducted using the CT imaging system described above. A hybrid spectral model with a virtual filter was generated using the air scan data according to the methods described herein. That is, the virtual filter was calculated by calculating the LHR in accordance with method (300) to generate the hybrid spectral models represented by Equations (2) and (3). In this experiment, a lookup table mapping operator was generated for each X-ray detector in accordance with methods (500) and (520), depicted in FIGS. 5A-5B.

During an imaging session, a CATPHAN® 600 uniformity phantom module was scanned at 120 kVp, with a 150 mA tube current, while rotating the CT imaging system at 30 RPM. CT projection data was calculated from the acquired X-ray intensity data. The CT images in FIGS. 7A-7C were reconstructed using FDK with 3-D backprojection. FIG. 7A depicts an image where the acquired CT projection data was not corrected for beam-hardening artifacts, FIG. 7B depicts an image where the acquired CT projection data was corrected for beam-hardening artifacts using an ideal spectral model that does not include a virtual filter (e.g., Equation (1)), and FIG. 7C depicts an image where the acquired CT projection data was corrected for beam-hardening artifacts using a hybrid spectral model with the virtual filter (e.g., Equations (2) and (3)). In addition, the mean CT number of an inner circled region and an outer circled region at the same locations in all of the images are indicated in each of FIGS. 7A-7C. The image in FIG. 7A has a distinct ring artifact (as indicated by the labeled arrow), a light-shaded circular band or halo that is the result of a bowtie filter artifact, and also a pronounced cupping artifact that appears as a darkened disk surrounding the ring artifact. The mean CT number of the inner circled region (62 HU) differs greatly from the mean CT number of the outer circled region (26 HU), with a difference of about 36 HU. The image in FIG. 7B also has a similar ring artifact, but the bowtie filter artifact is reduced and the cupping artifact is also reduced. The difference between the mean CT number of the inner circled region (27 HU) and the outer circled region (16 HU) is 9 HU, which is a reduction as compared with the image of FIG. 7A. While the cupping, bowtie filter, and ring artifacts present in FIG. 7A were reduced somewhat in FIG. 7B, these artifacts were even further reduced in FIG. 7C using the beam-hardening correction methods described herein. As seen in the image of FIG. 7C, the ring artifact is greatly reduced or eliminated, and there is little if any visible bowtie filter and cupping artifacts. The difference between the mean CT number of the inner circled region (20 HU) and the outer circled region (19 HU) is 1 HU, which is an even further reduction as compared with the image of FIG. 7B. Furthermore, the uniformity of the CT image was improved in FIG. 7C as compared to FIG. 7A. Without beam-hardening correction, the overall image of FIG. 7A had a CT number uniformity of 36 HU, but with the beam-hardening correction in accordance with the methods described herein, the overall image of FIG. 7C had a CT number uniformity of 1 HU.

The invention claimed is:

1. A method for phantom-less calibration of a CT imaging system to reduce beam-hardening artifacts, the method comprising:

acquiring a first set of X-ray intensity data for each X-ray detector of a CT imaging system during a first air scan at a first effective mean energy;

acquiring a second set of X-ray intensity data for each X-ray detector of the CT imaging system during a second air scan at a second effective mean energy that is higher than the first effective mean energy;

calculating a virtual filter for each X-ray detector of the CT imaging system using the first and second set of X-ray intensity data, wherein each virtual filter is made of a selected material and has a thickness and wherein calculating the virtual filter for each X-ray detector comprises calculating the thickness of the virtual filter by calculating a low-to-high ratio ($LHR_{meas}^i$) of the X-ray intensity data ($I_{lower}^i$) acquired at the first lower effective mean energy to the X-ray intensity data acquired at the second higher effective mean energy ($I_{higher}^i$):

$$LHR_{meas}^i = \frac{I_{lower}^i}{I_{higher}^i}$$

and calculating the thickness ($T_{vir}^i$) of the virtual filter for each of the i X-ray detectors, $$T_{vir}^i \approx \frac{\int S_{eff-L}^i(E)dE - LHR_{meas}^i \int S_{eff-H}^i(E)dE}{\int S_{eff-L}^i(E)\mu_{vir}(E)dE - LHR_{meas}^i \int S_{eff-H}^i(E)\mu_{vir}(E)dE}$$

where $S_{eff-L}^i(E)$ is a spectrum of the CT imaging system at the first lower effective mean energy, $S_{eff-H}^i(E)$ is a spectrum of the CT imaging system at the second higher effective mean energy, and $\mu_{vir}(E)$ is an attenuation coefficient of virtual filter of the selected material; and calculating a mapping operator for each X-ray detector of the CT imaging system, wherein the mapping operator comprises a hybrid spectral model that uses the virtual filter to convert a polychromatic projection value to a monochromatic projection value.

2. The method of claim 1, wherein calculating a mapping operator comprises generating a lookup table LUT having k monochromatic projection values $p_m$ that have been calculated from a discrete set of k polychromatic projection values $p_p^{discrete}$ each separated by a discretization step size s using the hybrid spectral model.

3. The method of claim 2, wherein the lookup table is a first lookup table LUT_1 for a first CT scan energy level, and the mapping operator further comprises a second lookup table LUT_2 for a second CT scan energy level, wherein the method further comprises calculating k' monochromatic projection values $p'_m$ that have been calculated from a second discrete set of k' polychromatic projection values $p'_p{}^{discrete}$ each separated by a discretization step size s' using the hybrid spectral model.

4. The method of claim 1, wherein the hybrid spectral model $mS_{eff}^i(E)$ is a combination of an ideal spectral model $S_{eff}^i(E)$ and the virtual filter having the thickness ($T_{vir}^i$) and the attenuation coefficient $\mu_{vir}(E)$:

$$mS_{eff}^i(E) = S_{eff}^i(E)\exp(-\mu_{vir}(E) \times \alpha T_{vir}^i)$$

where α is a scaling factor.

5. The method of claim 4, wherein calculating the mapping operator comprises iteratively calculating a monochromatic projection value ($p_m$) that corresponds to a polychromatic projection value ($p_p$) based on the hybrid spectral model:

$$p_p = -\ln\left(\frac{\int mS_{eff}^i(E)\exp(-\mu'_{obj}(E)p_m)dE}{\int mS_{eff}^i(E)dE}\right)$$

where $\mu'_{obj}(E)$ is a normalized attenuation coefficient $$\left(\frac{\mu_{obj}(E)}{\mu_{obj}(\overline{E})}\right)$$

of a scanning subject.

6. The method of claim 5, wherein $\mu'_{obj}(E)$ is a normalized attenuation coefficient of water, $\mu_{vir}(E)$ is the attenuation coefficient of aluminum, and the scaling factor α is 1.

7. The method of claim 1, wherein the CT imaging system comprises a rotatable gantry, an imaging X-ray source mounted to the gantry, and the X-ray detectors are mounted to the gantry opposite the imaging X-ray source, and wherein acquiring the first set of X-ray intensity data comprises rotating the gantry during the first air scan.

8. The method of claim 7, wherein acquiring the second set of X-ray intensity data comprises rotating the gantry during the second air scan.

9. The method of claim 8, wherein the first energy is 80 kVp and the second energy is 140 kVp.

* * * * *